United States Patent [19]

Kunde et al.

[11] Patent Number: 5,410,081
[45] Date of Patent: Apr. 25, 1995

[54] PROCESS FOR THE PREPARATION OF AMINO-SUBSTITUTED THIOETHERS

[75] Inventors: Klaus Kunde, Neunkirchen-Seelscheid; Karl-Josef Herd, Odenthal, both of Germany

[73] Assignee: Bayer Aktiengesellschaft, Leverkusen, Germany

[21] Appl. No.: 265,525

[22] Filed: Jun. 24, 1994

[30] Foreign Application Priority Data

Jul. 2, 1993 [DE] Germany ............... 43 22 053.3
Sep. 28, 1993 [DE] Germany ............... 43 32 978.0

[51] Int. Cl.$^6$ ............... C07C 209/62; C07C 209/68
[52] U.S. Cl. ............... 564/413; 564/391; 564/440; 564/487; 564/501
[58] Field of Search ............... 564/413, 487, 391, 440, 564/501

[56] References Cited

U.S. PATENT DOCUMENTS

3,950,542  4/1976  Kalopissis et al. ............... 424/316

OTHER PUBLICATIONS

Poindexter et al., J. Org. Chem., vol. 57(1992) pp. 6257–6265.
Journal of Medicinal Chemistry, vol. 20, No. 11, Nov. 1977, pp. 1357–1362.
U. Petersen: Cyclische Carbamidsaure Ester., Houben-Weyl (1983) vol. E4, pp. 192–211.
Inorganic Chemistry, vol. 25, 1986, pp. 4175–4180.
Monatshefte Für Chemie, vol. 110, 1979, pp. 767–789.

*Primary Examiner*—Richard L. Raymond
*Attorney, Agent, or Firm*—Sprung Horn Kramer & Woods

[57] ABSTRACT

Compounds of the formula (I)

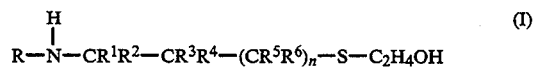

are prepared by reacting 2-mercaptoethanol with compounds of the general formula (II)

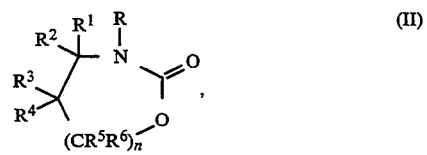

the substituents having the definition given in the description.

11 Claims, No Drawings

PROCESS FOR THE PREPARATION OF AMINO-SUBSTITUTED THIOETHERS

The invention relates to a new process for the preparation of amino-substituted thioethers. Compounds of this type and their preparation are known fundamentally from Journal of Medicinal Chemistry, 1977, Vol. 20, Soloway, Chemo-Immuno-Therapy of Cancer, pp. 1357 ff. Furthermore, J. Org. Chem. 1992, 57, Poindexter, pp. 6257–6265 discloses the use of 2-oxazolidinones for the aminoethylation of aromatic compounds.

The present invention relates to a process for the preparation of compounds of the general formula (I)

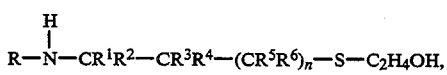

in which

R, $R^1$-$R^6$ independently of one another denote hydrogen, $C_1$-$C_4$-alkyl, OH-, $C_1$-$C_4$-alkoxy- or $SO_3H$-substituted $C_1$-$C_4$-alkyl, phenyl, benzyl, or halogen-, $C_1$-$C_4$-alkoxy- or $SO_3H$-substituted phenyl or benzyl, and n represents 0 or 1;

characterized in that 2-mercaptoethanol is reacted with compounds of the general formula (II)

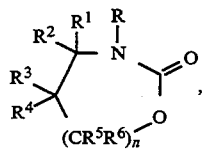

in which

R, $R^1$-$R^6$ and n have the meaning given above.

The reaction is preferably carried out at a temperature of from 50° C. to 250° C., preferably from 60° C. to 200° C.

The reaction can optionally be carried out in a solvent.

Solvents which can be used are all those whose $pK_a$ value is distinctly lower than that of 2-mercaptoethanol and which do not themselves react with 2-mercaptoethanol, for example hydrocarbons, ethers, alcohols, carboxamides, sulphoxides and sulphones; .mines are excepted.

Although the reaction of 2-oxazolidinones with thiophenols is known, there has been no successful reaction with alkanethiols to give the 2-(alkylmercapto)-ethylamines (G.S. Poindexter et al., J. Org. Chem. 1992, 57, 6257–6265).

Some of the compounds of the formula (II) are known; they are prepared by processes as described in Houben-Weyl, Vol. E4 (1983), pp. 192–211.

Examples of suitable compounds of the formula II for n=0 are 1-oxo-1,3-oxazolidine (2 -oxazolidinone),
5-methyl-2-oxo-1,3- oxazolidine,
3-methyl- 2-oxo-1,3- oxazolidine,
3-phenyl- 2-oxo-1,3- oxazolidine,
3-benzyl- 2-oxo-1,3- oxazolidine,
4-phenyl- 2-oxo-1,3- oxazolidine,
5-phenyl- 2-oxo-1,3- oxazolidine,
3,4-diphenyl-2-oxo-1,3-oxazolidine,
3,5-diphenyl-2-oxo-1,3-oxazolidine,
3,4-dimethyl-5-phenyl-2-oxo-1,3 -oxazolidine,
3-phenyl-4-hydroxymethyl-2-oxo-1,3-oxazolidine,
3,5-dimethyl-2-oxo-1,3-oxazolidine,
3-ethyl-2 -oxo-1,3 -oxazolidine,
4-ethyl-2 -oxo-1,3 -oxazolidine,
and for n=1 are
tetrahydro [1,3 ]oxazin- 2 -one:,
3-methyl-tetrahydro [1,3]oxazin-2-one,
3-phenyl-tetrahydro [1,3]oxazin-2-one,
3-benzyl-tetrahydro [1,3]oxazin-2-one,
4-methyl-tetrahydro [1,3]oxazin-2-one,
6-methyl-tetrahydro [1,3]oxazin-2- one.

The preferred process is for the preparation of compounds of the formula (I)

in which

R represents hydrogen, methyl, ethyl, phenyl or benzyl and $R^1$-$R^6$ independently of one another denote hydrogen, methyl and phenyl, and in particular represent hydrogen.

A further preferred embodiment of the process is characterized in that the reaction of compounds of the formula (II) is carried out with 2-mercaptoethanol and a base, preferably with an equimolar quantity of base in relation to the compound of the formula (II) in which R, $R^1$-$R^6$ and n have the above meanings. Examples of bases which can be used are alkali, alkali metal carbonates, alkali metal alkoxides or tertiary amines, but preferably sodium alkoxides and potassium alkoxides.

The preferred temperature for this base-induced variant of the process is preferably from 50 to 150° C., in particular from 60 to 110° C., and examples of the solvents employed are N-methylpyrrolidone, caprolactam, N-methylcaprolactam, cyclohexanol, dimethyl sulphoxide, dimethyl sulphone, sulpholane, methanol, ethanol, n-propanol, isopropanol, n-butanol, see-butanol, isobutanol, tertbutanol, water or mixtures thereof, especially methanol, ethanol, isopropanol and/or water.

This base-induced variant of the process is very particularly preferred for the preparation of compounds of the formula (I) in which n=0.

Also preferred is an embodiment for the preparation of compounds of the formula (I), in which n=0 and R and $R^1$-$R^4$ have the meaning given above, which is characterized in that 2-mercaptoethanol is reacted with compounds of the formula (II) in which n=0 and R and $R^1$-$R^4$ have the above meaning.

This variant of the process is carried out preferably at a temperature of from 100 to 250° C., in particular at from 150 to 200° C., and possibly in a solvent but preferably solvent-free. Examples of suitable solvents which can be used for the latter process are: mesitylene, naphthalene, 1-methylnaphthalene, 2-methylnaphthalene, decaline, tetraline, o-dichlozobenzene, nitrobenzene, biphenyl, diphenyl ether, 1-hexanol, 1-heptanol, 1-octanol, 2 octanol, ethylene glycol, diethylene glycol, diethylene glycol monomethyl ether, diethylene glycol monoethyl ether, glycerol, N-methylpyrrolidone, caprolactam, Nme thylcaprolactum, cyclohexanol, dimethyl sulphoxide, dimethyl sulphone and sulpholane, especially N-methylpyrrolidone, caprolactam and sulpholane.

The 2-(2'-aminoalkylmercapto)-ethanols prepared in accordance with the invention can be used as intermediates for pharmaceuticals, and pesticides, but in particular for dyes.

The process according to the invention particularly preferably employs the following compounds of the formula II: 3-phenyl - 2- oxazolidinone, 3-methyl - 2- oxazolidinone, 2-oxazolidinone, 3-methyl-tetrahydro [1,3]-oxazin-2-one or 3- phenyl - tetrahydro [1,3]oxazin - 2- one.

EXAMPLE 1

78.1 g of 2-mercaptoethanol and 163 g of 3-phenyl-2-oxazolidinone are heated at 160° C. under $N_2$ for 5 hours. 2- (2'-Phenylaminoethylmercapto) ethanol is obtained in almost quantitative yield as a pale yellow oil whose H NMR spectrum shows the following signals: (solvent $D_6$-DMSO)

$\delta 2.58$–2.75 ppm, 6H, m; $\delta 3.22$ ppm, 2H, t; $\delta 4.80$ ppm, 1H, s; $\delta 6.50$–6.61 ppm, 3H, m; $\delta 7.05$ ppm, 2H, d.

EXAMPLE 2

156.2 g of 2-mercaptoethanol and 202 g of 3-methyl-2-oxazolidinone are heated at 160° C. under $N_2$ for 5 hours. The 2-(2'-methylaminoethylmercapto) ethanol is distilled under reduced pressure. A colourless oil is obtained; b.p. 5–6.5 mm = 124° C. to 130° C.

EXAMPLE 3

78.1 g of 2-mercaptoethanol and 87 g of 2-oxazolidinone are heated at boiling in 100 ml of diethylene glycol monomethyl ether for 5 hours. First the solvent and then the 2-(2'-aminoethylmercapto) ethanol are distilled under reduced pressure; b.p. 3 nun. = 117° C. to 119° C.

EXAMPLE 4

177 g of 3-phenyl-tetrahydro [1,3]oxazin-2-one are stirred with 200 ml of ethanol, 70 g of sodium ethoxide and 80 g of mercaptoethanol are added, and the mixture is heated under reflux conditions for 7 hours. After the end of reaction the ethanol is distilled off and the residue is stirred with 200 ml of water. The pale yellow oil which has separated out is isolated and characterized as 2-(3'-phenylamino-n-propylmercapto)ethanol.

$^1$H NMR ($D_6$-DMSO): $\delta 1.8$ ppm, 2H, m; $\delta 2.6$ ppm, 4H, m; $\delta$ 3.09 ppm, 2H, q; $\delta 3.55$ ppm, 2H, q; $\delta 4.8$ ppm, 1H, t; $\delta$ 5.56 ppm, 1H, t; $\delta 6.54$ ppm, 3H, m; $\delta 7.09$ ppm, 2H, m.

EXAMPLE 5

15 74 g of N-methyl-1,2-ethanolamine, 130 g of diethyl carbonate and 15 g of sodium ethoxide are slowly heated at 90° C. in 50 ml of ethanol. Ethanol is subsequently distilled off until a bottom temperature of 110° C. is reached. 72 g of mercaptoethanol are added to the hot melt, and the mixture is heated to 160° C. over the course of four hours. The resulting 2-(2'-methylamino) ethylmercapto) ethanol is purified by distillation at from 140 to 145° C./20 mm.

$^1$H NMR (De-DMSO/$D_2$O): $\delta 2.26$ ppm, 3H, s; $\delta 2.52$–2.65, 6H, m; $\delta 3.50$, 2H, t.

We claim:

1. A process for the preparation of a compound of the general formula ( I )

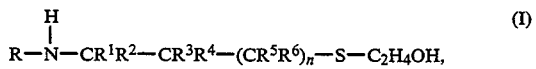

in which

R, $R^1$-$R^6$ independently of one another denote hydrogen, $C_1$-$C_4$-alkyl, OH-, $C_1$-$C_4$-alkoxy or $SO_3H$-substituted $C_1$-$C_4$-alkyl, phenyl, benzyl, or halogen-, $C_1$-$C_4$-alkoxy- or $SO_3H$ substituted phenyl or benzyl, and n represents 0 or 1, wherein 2-mercaptoethanol is reacted with a compound of the general formula (II)

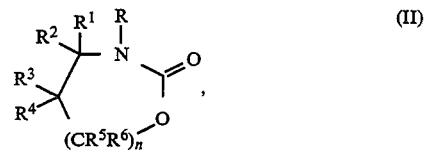

in which

R, $R^1$-$R^6$ and n have the meaning given above.

2. The process according to claim 1, wherein
R represents hydrogen, methyl, ethyl, phenyl or benzyl and
$R^1$-$R^6$ independently of one another denote hydrogen, methyl and phenyl.

3. The process according to claim 1, wherein the substituents $R^1$-$R^6$ denote hydrogen.

4. The process according to claim 1, wherein the reaction is carried out with a base.

5. The process according to claim 4, wherein the reaction is carried out at a temperature from 50 to 150° C.

6. The process according to claim 4, wherein an equimolar amount of base in relation to the compound of formula (II) is employed.

7. The process according to claim 4, wherein the reaction is carried out at a temperature from 60 to 100° C.

8. The process according to claim 1, wherein the reaction is carried out with compounds of the formula (II) where n=0.

9. The process according to claim 8, wherein the reaction is carried out at a temperature of from 100 to 250° C.

10. The process according to claim 8, wherein the reaction is carried out at a temperature from 150 to 200° C.

11. The process according to claim 1, wherein the compound of the formula (II) which is employed is 3-phenyl-2oxazolidinone, 3-methyl - 2- oxazolidinone, 2-oxazolidinone, 3-methyl-tetrahydro [1,3]oxazin-2-one or 3-phenyl-tetrahydro [1,3]oxazin-2-one.

* * * * *